United States Patent [19]

Schulz et al.

[11] Patent Number: 4,684,632

[45] Date of Patent: Aug. 4, 1987

[54] FORMULATION WITH SPECIAL 1,2-DIACYLGLYCERO-3-PHOSPHOCHOLINES FOR THE TREATMENT OF GASTROINTESTINAL DISORDERS

[75] Inventors: Volker Schulz, Cologne; Sigurd Leyck, Pulheim; Manfred Dürr, Pulheim-Dansweiler; Miklos Ghyczy, Cologne; Armin Wendel, Cologne; Jörg Hager, Cologne, Fed. Rep. of Germany

[73] Assignee: A. Nattermann & CIE. GmbH, Cologne, Fed. Rep. of Germany

[21] Appl. No.: 684,685

[22] Filed: Dec. 21, 1984

[30] Foreign Application Priority Data

Dec. 22, 1983 [DE] Fed. Rep. of Germany ....... 3346525

[51] Int. Cl.⁴ ............................................ A61K 31/685
[52] U.S. Cl. .................................... 514/78; 514/925; 514/926; 514/927; 514/928
[58] Field of Search ................ 514/78, 925, 926, 927, 514/928

[56] References Cited

U.S. PATENT DOCUMENTS

| | | |
|---|---|---|
| 3,169,094 | 2/1965 | Wretlind ............................... 514/78 |
| 4,263,286 | 4/1981 | Nakajima et al. ..................... 514/78 |
| 4,309,421 | 1/1982 | Ghyczy et al. ........................ 514/78 |
| 4,323,563 | 4/1982 | Takami et al. ........................ 514/78 |
| 4,332,795 | 6/1982 | Ghyczy et al. ........................ 514/78 |
| 4,378,354 | 3/1983 | Ghyczy et al. ........................ 514/78 |
| 4,421,747 | 12/1983 | Ghyczy et al. ....................... 514/78 |
| 4,425,276 | 1/1984 | Gunther .............................. 260/403 |
| 4,443,378 | 4/1984 | Gunther .............................. 268/403 |
| 4,452,743 | 6/1984 | Gunther .............................. 260/403 |
| 4,528,193 | 7/1985 | Ghyczy et al. ......................... 514/78 |

FOREIGN PATENT DOCUMENTS

| | | | |
|---|---|---|---|
| 54769 | 12/1981 | European Pat. Off. ............ 260/403 |
| 2097778 | 8/1979 | Fed. Rep. of Germany ........ 514/78 |
| 2343481 | 10/1977 | France ................................ 514/78 |
| 2039738 | 12/1978 | United Kingdom ................. 514/78 |

OTHER PUBLICATIONS

Puritan's Pride, Lecithin, p. 36, 1983.
The Merck Index, Ninth Edition, No. 5287, 1976, pp. 711–712.
Chemical Abstracts, vol. 80, 128122k, (1974).
Selecta 40, "Zytoprotektion wehrt peptische Ulzera ab", pp. 3361–3371, Oct. 3, 1983.
Science, 218, (1983), 1327–1329, "Role of Surface-Active Phospholipids in Gastric Cytoprotection".

*Primary Examiner*—Johnnie R. Brown
*Assistant Examiner*—John W. Rollins, Jr.
*Attorney, Agent, or Firm*—Burns, Doane, Swecker & Mathis

[57] ABSTRACT

Pharmaceutical formulations for the treatment of gastrointestinal disorders, which contain as the active component an effective gastrointestinal disorder alleviating amount of a 1,2-diacylglycero-3-phosphocholine in which 75–86% by weight of the acyl radicals are unsaturated fatty acid radicals having a chain length of 16, 18 or 20 carbon atoms. The mixtures of fatty acid radicals in the acyl groups in the 1- and 2-positions preferably have different compositions. The formulations can also contain other active compounds, in particular those which display injurious gastrointestinal side effects.

17 Claims, No Drawings

FORMULATION WITH SPECIAL 1,2-DIACYLGLYCERO-3-PHOSPHOCHOLINES FOR THE TREATMENT OF GASTROINTESTINAL DISORDERS

BACKGROUND OF THE INVENTION

The present invention relates to new pharmaceutical formulations for the treatment of gastrointestinal disorders.

About 10% to 20% of people suffer once or several times in their life from a peptic ulcer of the stomach or of the duodenum or from other inflammatory gastrointestinal lesions. There are a wide variety of causes, for example including endogenous cytotoxic substances, such as gastric acid and bile acids, or exogenous factors, such as ethanol or medicaments. Thus, the gastrointestinal tract is among the organ systems which are most frequently affected by the side effects of medicaments. In particular, non-steroidal antiinflammatory agents lead to erosion and ulceration of the stomach.

At present, the treatment of mucosal damage (ulcers) of the stomach and of the duodenum is primarily based on the elimination of aggressive factors, such as blocking acid and pepsin by acid neutralization (antacids, such as, for example, aluminum hydroxides, calcium carbon, hydrotalcite, magnesium hydroxide, sodium bicarbonate and others), inhibition of secretion (anticholinergics, $H_2$-antagonists, such as, for example, cimetidine or ranitidine, vagotomy or distal gastric resection) or increased rate of elimination (metoclopramide, sulpiride); and prevention of cytotoxic effects of certain constituents (bile acids, lysolecithin) of the duodenal juice in the stomach by absorption (cholestyramine, antacids) or increased rate of elimination (metoclopramide, sulpiride).

In addition, film-forming agents, such as sulfated disaccharides (sucralfate), are used.

Thus, treatment to date is primarily based on a reduction in the activity of gastric acid and pepsin. This in intended to prevent the "breakthrough" of the mucosal barrier. However, the consequence of this treatment is that there are also adverse effects on the digestion of food, which in turn results in further disturbance of and strain to the gastrointestinal tract.

A number of other disadvantages of these therapeutic agents used nowadays are known. Thus, the acid gastric juice itself also has protective functions, for example in the resistance to bacteria. This natural protection is lost. Moreover, antacids, depending on their composition, can cause constipation or the formation of stones or inhibit the absorption of minerals and drugs. Anticholinergic agents and the recently very frequently used $H_2$-antagonists have similar effects and, moreover, bring about more extensive disturbances. These medicinal agents are absorbable and thus effective systemically throughout the body, and are associated with a large number of side effects. For example, anticholinergic agents bring about dry mouth and disturbances of accommodation; $H_2$-antagonists cause headaches, diarrhea, joint and muscle pain, fatigue, dizziness, loss of hair, sexual behavioral disturbances, liver damage and others.

It has also been proposed, in European Pat. No. 92,121, to cover the gastric mucosa with an amphoteric phospholipid surfactant in order to prevent damage. These considerations are based on the protective effect of natural surfactants in the lung. The nature of these "surfactants" has been examined in detail, for example: B. H. Hills et al., J. Appl. Physiol.: Environ. Exercise Physiol. 1982, 53 (1), 119–123; 1982, 53 (2), 463–469; 1983, 54 (2), 420–426; Respiration Physiology 1983, 51, 79–93; L. M. Lichtenberger, Scienced 219 (1983), 1327–1329.

The most important components which have been identified are:
dipalmitoylphosphatidylcholine (DPPC),
dipalmitoylphosphatidylglycerol (DPPG),
dipalmitoylphosphatidylethanolamine (DPPE) and
sphingomyelin (SP).
Combinations, such as, for example,
DPPC:DPPE:DPPG:SP (5:2:2:1)
DPPC:DPPE:DPPG (5:2:2)
DPPC:DPPE (1:1)
DPPC:DPPG (1:1) or
DPPC:DPPE:SP
are particularly advantageous.

However, in order to permit film formation, it is important (B. A. Hills et al., A.J. Physiol. 244 (Gastrointest. Liver Physiol 7), G561–G568, 1983) that the fatty acid radicals in the phospholipids are able to extend in a straight line. Thus, only saturated fatty acid radicals, in particular palmitic acid, are suitable.

However, the use of this type of "surfactant" for the therapy of mucosal damage involves a number of difficulties, as follows:

Much effort is involved in obtaining this type of natural surfactants of complex structure.

On therapeutic use of this type of surfactant, the predominantly saturated fatty acid radicals in the phospholipid must be regarded as a great problem because of their unfavorable effect on lipid metabolism and the risk of atherosclerosis resulting from this (M. Rosseneu et al., Atherosclerosis 32 (1979) 141–153).

The formation of a protective film in the stomach is very difficult. Extrapolation of the function of the surfactants in the pulmonary alveoli to the mucosa of the gastrointestinal tract is impossible because of the anatamical and physoilogical differences between the monolayer, flat endothelium which forms a good substrate for a stable molecular film of lipid. In respect of function, merely the exchange of small gas molecules ($O_2$, $CO_2$) takes place there, and these diffuse through the lipid film without difficulty.

In contrast, intensive secretion and absorption processes take place in the stomach and intestines. The latter processes relate, in particular, to large water-soluble molecules as well, so that film formation is hardly possible.

Present-day ulcer treatment is a symptomatic, and by no means curative, treatment. At the most, it cures the ulcer, but it does not cure the ulcerative disorder.

Thus, a treatment which increases the protective properties of the mucosa would be desirable as an alternative aim of treatment. The first active compound disclosed which stimulated the protective properties of the mucosa was carbenoxolone. However, because of pronounced side effects (retention of sodium and water, hypokaliemia), only restricted use is possible.

The properties of the prostaglandins which have been well documented experimentally, such as the increase in the secretion of bicarbonate and mucus, in the blood flow in the mucosa and in the promotion of epithelial cell maturation and of gastric emptying indicate that the therapeutic principle of cytoprotection would be fulfilled in an ideal manner by administration of this group of active compounds.

However, the long-lived $PGE_2$ analogs which have been clinically tested to date were associated with the disadvantage of considerable systemic side effects.

In contrast, the natural prostaglandins act as so-called local hormones in the digestive tract as in other organs. This means that they do not reach their site of action via the blood stream but are formed in the immediate neighborhood of, or even directly in, the tissues in which they display their short-lived action.

Thus, it is worthwhile aiming at a therapeutic means of treatment which favors the physiological synthesis, locally in the intestinal mucosa, of the prostaglandins which protect the mucosa. From theoretical considerations, the substrates of prostaglandin synthesis which are particularly suitable for this are those which accumulate rapidly and persistently in the gastrointestinal mucosa on oral administration.

The object of the present invention is to make available pharmaceutical formulations for the treatment of gastrointestinal disorders, which accumulate rapidly and persistently in the gastrointestinal mucosa on oral administration and thus can be used as a substrate for the synthesis of protaglandins which protect the mucosa.

SUMMARY OF THE INVENTION

The present invention is a pharmaceutical formulation for the treatment of gastrointestinal disorders. The active component of the formulation is an effective gastrointestinal disorder alleviating amount of a 1,2-diacylglycero-3-phosphocholine in which 75–86% by weight of the acyl radicals are unsaturated fatty acid radicals or mixtures thereof with a chain length of 16, 18 or 20 carbon atoms.

DETAILED DESCRIPTION OF THE INVENTION

It has been found, surprisingly, that special 1,2-diacylglycero-3-phosphocholines, defined as 1,2-diacylglycero-3-phosphocholines in which acyl represents predominantly unsaturated fatty acid radicals having 16 and/or 18 and/or 20 carbon atoms, are outstandingly suitable for the treatment of gastrointestinal disorders. The suitable special 1,2-diacylglycero-3-phosphocholines have 75–86% of unsaturated fatty acid radicals. Preferred 1,2-diacylglycero-3-phosphocholines are those which contain as the fatty acid radicals linoleic acid or mixtures of fatty acids of the following composition:

10–14% by weight of palmitic acid
3–5% by weight of stearic acid
8–12% by weight of oleic acid
62–68% by weight of linoleic acid
4–6% by weight of linolenic acid the individual contents being selected so that they always amount to 100%.

Very particularly preferred 1,2-diacylglycero-3-phosphocholines are those in which the 1- and 2-acyl radicals consist of different mixtures of fatty acid radicals.

In these preferred 1,2-diacylglycero-3-phosphocholines, the acyl radical in the 1-position consists of the following fatty acid radical mixtures:

22–26% by weight of palmitic acid
6–9% by weight of stearic acid
8–12% by weight of oleic acid
50–54% by weight of linoleic acid
4–6% by weight of linolenic acid and the acyl radical in the 2-position consists of the following fatty acid radical mixtures:

1–2% by weight of palmitic acid
0–1% by weight of stearic acid
8–12% by weight of oleic acid
78–85% by weight of linoleic acid
5–8% by weight of linolenic acid the individual contents being selected so that they always amount to 100%.

The 1,2-diacylglycero-3-phosphocholines correspond to the general formula

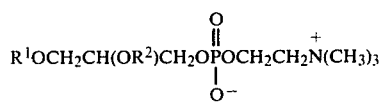

in which $R^1$ and $R^2$, which can be identical or different, denote the radicals

in which
L = 1, 4, 7, 8 or 10
m = 0, 1, 2, 3 or 4
n = 2 or 6 such as, for example, the following radicals
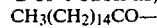

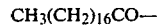

The pharmaceutical formulations with special 1,2-diacylglycero-3-phosphocholines can, where appropriate, contain up to 20% of other 1,2-diacylglycero-3-phosphates or their mixtures, such as, for example, 1,2-diacylglycero-3-phosphoethanolamine, 1,2-diacylglycero-3-phosphoinositol, 1,2-diacylglycero-3-phosphoserine, 1,2-diacylglycero-3-phosphoglycerol, but in particular 1,2-diacylglycero-3-phosphoethanolamine, the acyl radicals having the same composition as indicated for the 1,2-diacylglycero-3-phosphocholines. However, 1,2-diacylglycero-3-phosphocholines having the following composition of fatty acids 20–10% by weight of palmitic acid
5–4% by weight of stearic acid
10–12% by weight of oleic acid
62–68% by weight of linoleic acid
3–6% by weight of linolenic acid are preferred. Very particularly preferred 1,2-diacylglycero-3-phosphocholines are those in which the 1- and 2-acyl radicals consist of different mixtures of fatty acid radicals. In these preferred 1,2-diacylglycero-3-phosphocholines, the acyl radical in the 1-position consists of the following fatty acid mixtures 22–26% by weight of palmitic acid
7–9% by weight of stearic acid
12–9% by weight of oleic acid
54–50% by weight of linoleic acid
5–6% by weight of linolenic acid and the acyl radical in the 2-position consists of the following fatty acid radical mixtures 1–3% by weight of palmitic acid
0–2% by weight of stearic acid
8–12% by weight of oleic acid
85–75% by weight of linoleic acid
6–8% by weight of linolenic acid, the individual contents being selected so that they always amount to 100%.

These 1,2-diacylglycero-3-phosphocholines can be obtained by processes known per se, in particular from soybeans.

As whole-body autoradiographs show, the special 1,2-diacylglycero-3-phosphocholines accumulate rapidly and persistently in the gastrointestinal mucosa after oral administrtion. It has been demonstrated in animal experiments that pretreatment which special 1,2-diacylglycero-3-phosphocholines impressively protects the experimental animals from damage to the gastric mucosa initiated by agents which irritate the mucosa.

Clinical investigations have been carried out on 9 patients. This entailed the recording of 7 characteristic subjective parameters (heartburn, epigastric pain, bloating, loss of appetite, retching, nausea and hiccups), which occur in association with mucosal erosions and ulcerations in the stomach and duodenum, before and after treatment with 1,2-diacylglycero-3-phosphocholine. The documentation was semiquantitative, taking into account the intensity of the symptoms. In 8 of 9 patients (including 4 taking non-steroidal antirheumatic agents, 1 taking cytostatic agents, 1 with gastric stump gastritis, 1 with bilious reflux, 1 with chronic recurrent peptic ulcer) considerable improvements, some of which were dramatic, in the symptoms were recorded within 1–4 days of treatment. No side effects or adverse effects on the other drug treatment occurred.

As shown by the animal experiments and clinical investigations, both oral and parenteral treatment with special 1,2-diacylglycero-3-phosphocholine lead to a lasting protection of the gastric mucosa. The cytoprotective effect may be explained as local stimulation of prostaglandin synthesis by reason of an accumulation of the 1,2-diacylglycero-3-phosphocholine in the mucosa. No systemic increases in the effects of prostaglandins, as have been observed in trials of long-lived $PGE_2$ analogs, were detected.

As shown by the investigations, both oral and parenteral administration of the special 1,2-diacylglycero-3-phosphocholines lead to a lasting protection of the gastric mucosa. This is particularly surprising and was unexpected from knowledge of European Pat No. 0,092,121, since the highly unsaturated 1,2-diacylglycero-3-phosphocholines according to the invention are unable, under physiological conditions, to form a serviceable protective film. Moreover, it was entirely unexpected that even parenteral administration leads to a lasting protection of gastric mucosa, since in this case film formation is completely ruled out.

The special 1,2diacylglycero-3-phosophocholines which are to be used according to the invention can be administered both orally and parenterally in doses of 0.2 to 150 mg, in particular 10–50 mg, per kg of body weight, once or several times a day. They can be administered for prophylaxis or therapy. Furthermore, administration is possible during treatment with medicaments which cause erosion and ulceration of the stomach. To prevent or eliminate damage to gastric mucosa caused by medicaments, it is possible to administer the 1,2-diacylglycero-3-phosphocholines before, during or after the treatment with these medicaments. Preferably, a pretreatment is carried out by administration of 1,2-diacylglycero-3-phosphocholine or by simultaneous administration of medicaments in order to prevent possible damage to the gastric mucosa due to the medicament.

In the treatment of severe ulceration, it is possible to use agents for treating ulcers, such as, for example, $H_2$-antagonists, to reduce or eliminate aggressive factors, and then to change to treatment with 1,2-diacylglycero-3-phosphocholines. This has the advantage that the side effects of the agents for treating ulcers are diminished.

It is advantageous to carry out a pretreatment with and/or simultaneous administration, in one dose or separate doses, of the special 1,2-diacylglycero-3phosphocholine particularly in the treatment of disorders with active compounds which are aggressive for the stomach and intestines, for example with cytostatics, such as methotrexate; antihypertensive agents, such as reserpine; tuberculostatics, such as rifampicin; or p-aminosalicyclic acid; antibiotics, such as penicillin; or analgesics or antiinflammatory agents, such as pyrazolones (phenylbutazone, oxyphenbutazone), salicyclic acid derivatives (salicyclic acid, salicylamide, acetylsalicylic acid benorilate, diflunisal); phenylalkanoic acids, such as, for example, ibuprofen, naproxen, alclofenac, ketoprofen, dichlofenac, fenoprofen, tolmetin, flurbiprofen, suprofen, indoprofen, carprofen, pirprofen, fenclofenac, sulindac, indomethacin, piroxicam, acemetacin, pimetacin, nambumetone and others.

For the administration of the special 1,2diacylglycero-3-phosphocholines, they are converted into suitable form, such as, for example, capsules, solutions, emulsions, tablets, powders, chewable capsules, drink ampoules or aqueous emulsions, as well as customary parenteral forms.

The special 1,2-diacylglycero-3-phosphocholines can be filled into soft gelatin capsules or, more advantageously, into hard gelatin capsules by processes known per se, for example by the process described in German Offenlegungsschrift 3,022,136, where appropriate with the addition of suitable auxiliaries and fillers. The soft or hard gelatin capsules can be swallowed whole or chewed.

For the production of the hard gelatin chewable capsules, the phospholipids are mixed with pharmaceutically inert vehicles, such as, for example, waxes, hydrogenerated oils, natural semisynthetic or synthetic triglycerides and their mixtures, such as cocoa butter and customary suppository compositions, for example based on triglycerides, such as, for example, Witepsol suppository compositions (see H. P. Fielder, Lexikon der Hilfsstoffe fur Pharmazie, Kosmtick und angrenzende Gebiete [Lexicon of Auxiliaries for Pharmacy, Cosmetics and Related Areas] 1971, Vol. 9, pp. 548–50 and 632–634); fatty alcohols; solid hydrocarbons, such as vaseline or hard paraffin; saturated fatty acids, such as lauric acid, myristic acid, palmitic acid, stearic acid; emulsifiers, such as ethoxylated triglycerides, polyethoxylated vegetable oils; fatty acid esters of sugars; silicones; gelatin; methyl cellulose; hydroxypropoxycellulose; hydroxypropylcellulose; polyethylene glycols; polyvinylpyrrolidone; polyvinyl alcohol; polyacrylic acid and its salts. Ethanol is added to the compositions in an amount such that the filling material obtained is free-flowing at room temperature or at a slightly elevated temperature under pressure, that is to say the product at this temperature has a viscosity which is just sufficiently low, or slightly lower, for transport under pressure, and this product can be filled into containers using known filling equipment with an accessory for liquid filling and with a heatable filling nozzle analogous to the method described in German Offenlegungsschrift 3,022,136.

It is also possible for the 1,2-diacylglycero-3-phosphocholines to be processed together with other agents for treating ulcers, or even with medicaments which have side effects damaging to the mucosa, by the process, by, for example, incorporating the latter in the viscous 1,2-diacylglycero-3-phosphocholine compositions before they are filled into containers, or metering the latter in the form of a powder or tablets into the 1,2-diacylglycero-3-phosphocholines after they have been filled into containers, it being possible for the ratio of 1,2-diacylglycero-3-phosphocholine and other active compounds to vary from 0.1:1 to 1:20.

It is necessary for the production of tablets and powder mixtures to convert the 1,2-diacylglycero-3-phosphocholines into solid form, this being extremely difficult because of the viscous properties of these substances. Solid formulations can be obtained by addition of 2–10% by weight of calcium chloride.

For the production of the solid formulations, the special 1,2-diacylglycero-3-phosphocholines are dissolved or emulsified, with the addition of customary auxiliaries, in water or an organic solvent, such as, for example, alcohols, such as methanol, ethanol or isopropanol, in hydrocarbons, such as hexane, chlorinated hydrocarbons or mixtures thereof, the calcium chloride is added, and the mixture is stirred, with gentle heating, and then the solvent is removed again in vacuo, whereupon a dry powder is obtained. The amount of calcium chloride added to these mixtures is 1–20%, but in particular 2–10%, relative to the amount by weight of 1,2-diacylglycero-3-phosphocholine.

Preferred solvents for the processing of 1,2-diacylglycero-3-phosphocholines are alcohols, in particular ethanol. Suspending agents are water or alcohols, such as methanol or ethanol.

Custmary processes are suitable for drying, such as vacuum drum drying, spray drying and freeze drying. The dried, comminuted 1,2-diacylglycero-3-phosphocholine/calcium chloride mixtures can, where appropriate, be comminuted or granulated by customary processes. It is advantageous to use for the stabilization of the products 0.1–2% by weight, relative to the amount of 1,2-diacylglycero-3-phosphocholine used, of a stabilizer or mixture of stabilizers, such as tocopherol acetate and/or ascorbyl palmitate.

The special 1,2-diacylglycero-3-phosphocholines can also be processed together with medicaments which have side effects damaging to the mucosa. These medicaments include, for example: cytostatics, chemotherapeutic agents, antibiotics, steroids, in particular steroidal and non-steroidal antiinflammatory agents.

The production of the solid oral drug forms, consisting of the medicinal agent or non-steroidal antiinflammatory agent and the special 1,2-diacylglycero-3-phosphocholine, can be carried out by a variety of processes, as follows:

Powder mixtures:

The medicinal agents which have been reduced to the appropriate particle size and a special 1,2-diacylglycero-3-phosphocholine/calcium chloride mixture are mixed, with the addition of customary pharmaceutical auxiliaries, and compressed to form tablets or filled into capsules.

Spray-dried compositions:

The solution or dispersion of the medicinal agent in organic solvents or water is mixed with a solution or emulsion of the special 1,2-diacylglycero-3-phosphocholine in organic solvents or water and the solution of calcium chloride in organic solvents or water and, where appropriate, other customary pharmaceutical auxiliaries, and the mixture is spray-dried. The resulting spray-dried composition, with the addition of other pharmaceutical auxiliaries, can either be compressed to form tablets or filled into capsules.

Coating compositions:

The solution or emulsion of the special 1,2diacylglycero-3-phosphocholine in organic solvents or water is mixed with a solution of calcium chloride in organic solvents or water and applied in a fluidized bed to the medicinal agent which has previously been reduced to the desired particle size. The resulting product in the form of a free-flowing powder is, with the addition of pharmaceutical auxiliaries, either compressed to form tablets or filled into capsules.

The rate of medicinal agent to 1,2-diacylglycero-3-phosphocholine/calcium chloride can vary in the weight ratio 1:0.1 to 1:20 depending on the therapeutic requirements. 50–250 mg, in particular 100 mg, of the 1,2-diacylglycero-3-phosphocholine/calcium chloride mixture is advantageously used per dose of the medicinal agent.

The advantage of the solid oral administration forms consisting of medicinal agents and the special 1,2-diacylglycero-3-phosphocholine/calcium chloride mixture over formulations consisting of medicinal agents and phospholipids, as are described in, for example, German Patent Specification No. 2,856,333, can be determined as follows: the production of emulsified phospholipid or 1,2-diacylglycero-3-phosphocholine from a solid oral drug form, consisting of medicinal agent and phospholipid or medicinal agent and 1,2-diacylglycero-3-phosphocholine/calcium chloride in gastric juice is determined by the USP dissolution test (rotating basket method, 100 rpm, 900 ml gastric juice, pH 1.2), material:

AS = phenylbutazone
PL = phosphatidylcholine
PC/CaCl$_2$ = 1,2-diacylglycero-3-phosphocholine/-calcium chloride (content: 6.43% CaCl$_2$)

Capsules each containing 200 mg of AS and 100 mg of PL or PC/CaCl$_2$

| Product | Amount of PL emulsified/dispersed after 30 minutes |
|---|---|
| 1. PL + AS | 37.7 mg |
| 2. PC/CaCl$_2$ + AS | 67.5 mg |

A further advantage of the preferred formulations according to the invention, consisting of medicinal agent and 1,2-diacylglycero-3-phosphocholine/calcium chloride, compared with drug forms consisting of medicinal agent and phospholipid is the possibility of combining high and requisite amounts of 1,2-diacylglycero-3-phosphocholine in the form of mixtures with CaCl$_2$ and medicinal agent by the process. For example, using the known fluidized bed process, the maximum mixing ratios obtainable with acetylsalicylic acid and phosphatidylcholine are only 1:0.2, while, in contrast, it is possible to prepare mixtures of acetylsalicylic acid with the special 1,2-diacylglycero-3-phosphocholine/calcium chloride with a ratio of more than 1:0.5.

Another great advantage comprises the powder-technological properties of the pharmaceutical formulations produced with the special 1,2-diacylglycero-3-phosphocholine/calcium chloride.

| Product | Settled density by DIN 53912 | Pourability by DIN 53916 |
|---|---|---|
| 1. ASA + PL | 227 g/l | not pourable |
| 2. ASA + PC/CaCl$_2$ | 257 g/l | cot$\phi$ = 1.43 |

ASA = acetylsalicylic acid
PL = phosphatidylcholine
PC = 1,2-diacylglycero-3-phosphocholine ASA = acetylsalicylic acid
PL = phosphatidylcholine
PC = 1,2-diacylglycero-3-phosphocholine The advantage of the powder-technological properties of the drug forms produced with 1,2-diacylglycero-3-phosphocholine/calcium chloride mixtures is attributable to the advantageous physical properties of the 1,2-diacylglycero-3-phosphocholine/calcium chloride mixture compared with the pure 1,2-diacylglycero-3-phosphocholine.

| Product Name | Settled density by DIN 53912 |
|---|---|
| 1. PC1 - milled | 229 g/l |
| 2. PC1/CaCl$_2$ - milled | 451 g/l |
| 3. PC1 - spray-dried | 88 g/l |
| 4. PC1/CaCl$_2$ - spray-dried | 222 g/l |
| 5. PC2 - milled | 230 g/l |
| 6. PC2/CaCl$_2$ - milled | 440 g/l |

PC1 = 1,2-diacylglycero-3-phosphocholine
PC2 = mixture of

80% 1,2-diacylglycero-3-phosphocholine
20% 1,2-diacylglycero-3-phosphoethanolamine.

If the intention is to administer the special 1,2-diacylglycero-3-phosphocholines together with other medicaments, it is also possible to coat medicament cores with the 1,2-diacylglycero-3-phosphocholine. Combination packs which contain the medicament to be administered and the formulations of the special 1,2-diacylglycero-3-phosphocholine are also possible.

In order to further illustrate the present invention and the advantages thereof, the following specific examples are given, it being understood that these examples are intended only to be illustrative without serving as a limitation on the scope of the present invention.

EXAMPLE 1

The following experiments were carried out to demonstrate the efficacy: Accumulation of special 1,2-diacylglycero-3-phosphocholine in the gastrointestinal mucosa.

Rates received 70 mg/kg of phosphocholine radiolabeled with $^3H$ (1,2-[9,10,11,12,13-$^3H_4$]-dilinolyl-sn-glycero-3-phosphocholine) by gavage. The radioactivity was $4.4 \times 10^6$ dpm of $^3H$ per animal. The rates were sacrificed 1.5, 3, 6 and 24 hours after administration by immersion in a mixture of acetone and dry ice ($-72°$ C.) under deep anesthesia with ether. Whole-body sections were prepared. The dry sections and 2 standards of different radioactivity were brought into contact with the photographic emulsion under a uniform pressure and exposed at $-20°$ C. The exposure lasted 47 days. It was shown by this autoradiographic imaging that the administered 1,2-diacylglycero-3-phosphocholine leads to a rapid and long-lasting accumulation in the gastrointestinal mucosa, which is evident from a very pronounced blackening of the stomach wall of the image.

EXAMPLE 2

Chemical damage to the mucosa.

An ulcerogenic dose of phenylbutazone (200 mg/kg, 5 ml/kg) was administered orally to male rats which had been fed only with white bread for 3 days and then fasted for 24 hours. The test substance was administered orally immediately thereafter. The animals were sacrificed by ether narcosis after 3.5 hours, and the stomachs were examined macroscopically. The ulceration was evaluated by the method of Takagi and Okabe (Jap. J. Pharmacol. 18, 9–18 (1968)) by means of an index.

| Test substance 120 mg/kg | Ulcer index control/experiment | | % change in the ulcer factor |
|---|---|---|---|
| PPC | 3.2 | 1.6 | −50.0% |
| DPPC | 1.9 | 1.2 | −36.8% |
| DPPC/DPPG 1:1 | 2.7 | 2.1 | −22.2% |
| DPPC/DPPE/DPPG/DPPI/Sph. 9:1:1:1:1 | 2.5 | 2.0 | −20.0% |

PPC = 1,2-diacylglycero-3-phosphocholine (acyl radicals about 62–68% of linoleic acid; 10–14% palmitic acid, 3–5% stearic acid, 8–12% oleic acid, and 4–6% linolenic acid)
DPPC = dipalmitoylphosphatidylcholine
DPPG = dipalmitoylphosphatidylglycerol
DPPE = dipalmitoylphosphatidylethanolamine
DPPI = dipalmitoylphosphatidylinositol
Sph = sphingomyelin The mixture DPPC/DPPE/DPPG/DPPI/Sph (9:1:1:1:1) corresponds to the most effective mixture from European Patent 0,092,121.

As is evident from the table, the 1,2-diacylglycero-3-phosphocholines according to the invention clearly led to the greatest inhibition of ulcer provocation.

EXAMPLE 3

1,2-Diacylglycero-3-phosphocholine emulsion.
1,2-Diacylglycero-3-phosphocholine 45.0 g
Dry glucose (starch hydrolyzate) 5.0 g
Flavorings 1.0 g
Preservatives 0.1 g
Water ad 100.0 g The 1,2-diacylglycero-3-phosphocholine is emulsified, with stirring, in the water to which the preservatives have been added, and then the dry glucose and flavorings are mixed in. The viscous emulsion is filled into tubes.

EXAMPLE 4

Hard gelatin capsules
(a) Composition and production of the filling material
1,2-diacylglycero-3-phosphocholine 76.0 kg
Hard fat 13.5 kg
Soya oil 8.5 kg
Ethanol 2.0 kg
Peppermint oil 0.04 kg are homogeneously mixed in a kneader.
(b) Filling into hard gelatin capsules.

The composition described under (a) is filled into hard gelatin capsules in a hard gelatin capsule machine having a filling point for liquid filling material at 60° C. Capsule size 0 elongated, dose 658 mg.

EXAMPLE 5

Drink ampoules
1,2-diacylglycero-3-phosphocholine 97.8 g
Combination Syrup 160.0 g
Mocha essence 2.0 ml
Marsala essence 3.2 ml
Purified water to 2000.0 ml The 1,2-diacylglycero-3-phosphocholine is dispersed, with stirring, in 1.4 l of water and then homogenized using a slit homogenizer. After addition of an aqueous solution of the combination syrup and the flavorings, the mixture is made up to 2 l with water and sterilized by filtration. The solution is then filled, under aseptic conditions, into injection vials (5 ml).

EXAMPLE 6

98 g of 1,2-diacylglycero-3-phosphocholine are dissolved, with warming, in ethanol, and mixed with a solution of 2 g of calcium chloride (anhydrous) in 50 ml of methanol. The solvents are removed in vacuo, and the resulting product is reduced, with the addition of 1% Aerosil 200, to a particle size $<100\ \mu$. The resulting powder is filled into capsules.

The mixture, with the addition of suitable auxiliaries, can also be compressed to form tablets.

EXAMPLE 7

90 g of 1,2-diacylglycero-3-phosphocholine are dissolved in 200 ml of chloroform, mixed with a solution of 10 g of anhydrous $CaCl_2$ in 200 ml of methanol, and the mixture is dried using a Buchi type 190 spray dryer.

The resulting product, with the addition of 1% Aerosil 200, is reduced to a particle size $<100\ \mu$, and can then be filled into capsules or compressed to form tablets.

EXAMPLE 8

94 g of a mixture of 80% by weight of 1,2-diacylglycero-3-phosphocholine and 20% by weight of 1,2-diacylglycero-3-phosphoethanolamine are dissolved in ethanol and mixed with a solution of 6 g of $CaCl_2$ (anhydrous) in 120 ml of ethanol. The solvent is removed in vacuo and the resulting product is processed in analogy to Example 6.

EXAMPLE 9

90 g of 1,2-diacylglycero-3-phosphocholine are emulsified in 500 ml of distilled water, mixed with a solution of 10 g of anhydrous $CaCl_2$ in 50 ml of distilled water and processed in analogy to Example 6.

EXAMPLE 10

Aqueous dispersion.
1,2-diacylglycero-3-phosphocholine/$CaCl_2$ 56.0 kg
Cream aroma 0.8 kg
Mocha chocolate essence 5.6 kg
Vanillin 0.4 kg
Dextrose 37.0 kg
Saccharin sodium 0.16 kg
are homogeneously mixed in a powder mixer.

To prepare the aqueous dispersion ready for drinking, immediately before use 12.5 g of powder mixture are added to 100 ml of water and the mixture is briefly shaken.

EXAMPLE 11

ASA tablets:
ASA-acetylsalicylic acid 300 mg
1,2-diacylglycero-3-phosphocholine/$CaCl_2$ 100 mg
Aerosil 200 20 mg
Na carboxymethylcellulose 20 mg
Hydrogenated castor oil 10 mg
Microcrystalline cellulose 150 mg The ingredients listed are mixed, compressed and provided in a customary manner with known tablet coating agents, for example cellulose acetate phthalate or hydroxypropylmethylcellulose phthalate.

EXAMPLE 12

ASA capsules:
ASA-acetylsalicylic acid, milled 100 300 mg
1,2-diacylglycero-3-phosphocholine/$CaCl_2$ 100 mg
Vehicle 15 mg A solution consisting of 90 g of 1,2-diacylglycero-3-phosphocholine/$CaCl_2$, 200 ml of chloroform and 10 g of anhydrous $CaCl_2$ with 200 ml of methanol is sprayed onto ASA, milled $<100\ \mu$, in a fluidized bed. The resulting free-flowing powder is filled into hard gelatin capsules containing 300 mg of ASA per capsule.

Example 13

Phenylbutazone tablets:
Phenylbutazone 200 mg
1,2-diacylglycero-3-phosphocholine/$CaCl_2$ 100 mg
Aerosil 200 30 mg
Na carboxymethylcellulose 20 mg
Hydrogenerated castor oil 10 mg
Microcrystalline cellulose 140 mg 200 g of phenylbutazone are dissolved in 500 ml of chloroform, 93.5 of the phospholipid are stirred in, and 6.5 g of $CaCl_2$, dissolved in 100 ml of methanol, are added. The resulting mixture is spray-dried, mixed with the remaining components, comminuted, compressed to form tablets each containing 200 mg of phenylbutazone, and coated in analogy to Example 11.

EXAMPLE 14

Indomethacin capsules:
Indomethacin 50 mg
1,2-diacylglycero-3-phosphocholine/$CaCl_2$ 100 mg
Vehicle 5 mg A solution consisting of 90 g of 1,2-diacylglycero-3-phosphocholine in 500 ml of isopropanol and 10 g of $CaCl_2$ in 100 ml of methanol is sprayed onto the milled indomethacin in a fluidized bed. The resulting powder is treated as described in Example 6.

EXAMPLE 15

Ibuprofen tablets:
Ibuprofen 200 mg
1,2-diacylglycero-3-phosphocholine/$CaCl_2$ 100 mg
Aerosil 200 30 mg
Microcrystalline cellulose 150 mg
Sodium carboxymethylstarch 20 mg
Magnesium strearate 10 mg
Preparation in analogy to Example 6.

EXAMPLE 16

Ibuprofen capsules:
Ibuprofen 200 mg 1,2-Diacylglycero-3-phosphocholine/CaCl$_2$ 100 mg
Vehicle 10 mg
Preparation in analogy to Example 12.

EXAMPLE 17

Sulindac tablets:
Sulindac 100 mg
1,2-Diacylglycero-3-phosphocholine/CaCl$_2$ 100 mg
Aerosil 200 20 mg
Microcrystalline cellulose 100 mg
Sodium carboxymethylcellulose 20 mg
Magnesium stearate 10 mg
Preparation in analogy to Example 11.

EXAMPLE 18

Naproxen capsules:
Naproxen 250 mg
1,2-Diacylglycero-3-phosphocholine/CaCl$_2$ 100 mg
Adsorbent 15 mg
Preparation in analogy to Example 12.

EXAMPLE 19

Diclofenac sodium tablets:
Diclofenac sodium 50 mg
1,2-Diacylglycero-3-phosphocholine 100 mg
Aerosil 200 15 mg
Microcrystalline cellulose 75 mg
Magnesium stearate 10 mg
Sodium carboxymethylcellulose 5 mg
Preparation in analogy to Example 11.

EXAMPLE 20

Tablets containing diclofenac:
Diclofenac sodium 1000 g
Avicel PH 102 1460 g
Aerosil 200 20 g
Magnesium stearate 25 g
Sodium carboxymethylstarch 25 g The mixture is compressed to form biconvex tablets each containing 150 mg of diclofenac sodium, and these are then coated with a coating composition consisting of 1,2-Diacylglycero-3-phosphocholine 15.0%
HPMC cps 7.5%
Colloidal SiO$_2$ 1.5%
Ethanol 38.0%
Methylene chloride 38.0% in amounts of about 100 mg per tablet.

EXAMPLE 21

Capsules containing diclofenac:
(a) Diclofenac sodium 1000 g
Avicel PH 102 460 g
Aerosil 200 10 g
Magnesium stearate 15 g
Sodium carboxymethylstarch 15 g
(b) Filling composition:
1,2-Diacylglycero-3-phosphocholine 9 kg
Polyethylene glycol 400 1 kg
Ethanol 0.3 kg The mixture is mixed homogeneously in a kneader at 60° C.

(c) Using the filling composition described under (b) in a hard gelatin capsule machine with accessory for filling liquids, 350 mg of the mixture are metered into each hard gelatin capsule of size 0. Then, using the same hard gelatin capsule filling equipment and a filling point for powders, 150 mg of the powder mixture described under (a) are metered into each capsule, and the capsule is closed.

The capsules contain 50 to 1500 mg of 1,2-diacylglycero-3-phosphocholine and 10–250 mg of non-steroidal antiinflammatory agents, the ratio of anti-inflammatory agents to 1,2-diacylglycero-3-phosphocholine advantageously being 1:0.1 to 1:10.

EXAMPLE 22

Capsules containing diclofenac:
(a) Diclofenac sodium 1000 g
Avicel PH 102 460 g
Aerosil 200 10 g
Magnesium stearate 15 g
Sodium carboxymethylstarch 15 g The substances are mixed homogeneously and compressed to form 150 mg tablets having a diameter of 6.5 mm.
(b) Filling composition
1,2-Diacylglycero-3-phosphocholine 76.5 kg
Witepsol 14.3 kg
Soya oil 9.2 kg
Ethanol 3.0 kg are homogeneously mixed in a kneader at 60° C.

(c) 500 mg of the filling composition described under (b) are filled into a hard gelatin capsule of size 0 in a hard gelatin capsule machine having a filling point for liquids. Then, using the same machine and a filling point for tablets, a tablet of the composition described under (a) is introduced into the capsule, and the capsule is closed.

EXAMPLE 23

Prednisolone tablets:
Prednisolone 5 mg
1,2-diacylglycero-3-phosphocholine/CaCl$_2$ 100 mg
Microcrystalline cellulose 60 mg
Aerosil 200 10 mg
Sodium carboxymethylstarch 15 mg
Magnesium stearate 10 mg
Preparation in analogy to Example 13.

EXAMPLE 24

Dexamethasone tablets
(9-Fluoro-16α-methylprednisolone)
Dexamethasone 0.5 mg
1,2-diacylglycero-3-phosphocholine/CaCl$_2$ 50.0 mg
Microcrystalline cellulose 30.0 mg
Aerosil 200 5.0 mg
Sodium carboxymethylstarch 4.5 mg
Magnesium stearate 10 mg
Preparation in analogy to Example 13.

EXAMPLE 25

Methotrexate tablets
Methotrexate 2.5 mg
1,2-diacylglycero-3-phosphocholine/CaCl$_2$ 100.0 mg
Microcrystalline cellulose 50.0 mg
Aerosil 15.0 mg Magnesium stearate 7.5 mg Preparation in analogy to Example 13.

EXAMPLE 26 p-Aminosalicylic acid tablets:
Sodium p-aminosalicylate.2H$_2$O 400.0 mg
1,2-diacylglycero-3-phosphocholine/CaCl$_2$ 100.0 mg
STA-RX 1500 (special corn starch) 45.0 mg Hydroxypropylcellulose 15.0 mg
Aerosil 10.0 mg
Preparation in analogy to Example 12.

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

What is claimed is:

1. A pharmaceutical formulation for the treatment of gastrointestinal disorders which occur in association with mucosal erosions and ulcerations in the stomach and duodenum, comprising as the active component an effective gastrointestinal disorder alleviating amount of a 1,2-diacylglycero-3-phosphocholine in which 75–86% by weight of the acyl radicals are a mixture of fatty acid radicals comprising
    10–14% by weight of palmitic acid
    3–5% by weight of stearic acid
    8–12% by weight of oleic acid
    62–68% by weight of linoleic acid
    4–6% by weight of linolenic acid.

2. The pharmaceutical formulation as claimed in claim 1, wherein the 1-acyl radical contains
    22–26% by weight of palmitic acid
    6–9% by weight of stearic acid
    8–12% by weight of oleic acid
    50–54% by weight of linoleic acid
    4–6% by weight of linolenic acid
and the 2-acyl radical contains
    1–2% by weight of palmitic acid
    0–1% by weight of stearic acid
    8–12% by weight of oleic acid
    75–85% by weight of linoleic acid
    5–8% by weight of linolenic acid
as the mixture of fatty acid radicals.

3. The pharmaceutical formulation as claimed in claim 1 which further contains up to 20% of at least one 1,2-diacylglycero-3-phosphate which is 1,2-diacylglycero-3-phosphoethanolamine, 1,2-diacylglycero-3-phosphoinositol, 1,2-diacylglycero-3-phosphoserine, or 1,2-diacylglycero-3-phosphoglycerol, the acyl radicals having the meaning indicated in claim 1.

4. The pharmaceutical formulation as claimed in claim 1 in the form of a hard gelatin capsule, which contains 50–500 mg of a 1,2-diacylglycero-3-phosphocholine per capsule.

5. The pharmaceutical formulation as claimed in claim 1 in the form of drink ampoules which contain an aqueous emulsion containing 5–60% of a 1,2-diacylglycero-3-phosphocholine.

6. The pharmaceutical formulation as claimed in claim 1 in the form of a solid formulation, in powder or tablet form, which contains a mixture of a 1,2-diacylglycero-3-phosphocholine and 2–10% of calcium chloride, relative to the phosphocholine.

7. A process for the preparation of a pharmaceutical formulation for oral use or oral administration, as claimed in claim 1, which comprises the 1,2-diacylglycero-3-phosphocholine being dissolved or emulsified in water or an organic solvent, calcium chloride, dissolved or suspended in water or an alcohol, being added at about 2–10% by weight based upon the weight of phosphocholine, the solvents being removed in vacuo, and the resulting product being dried.

8. A process for the preparation of a pharmaceutical formulation for oral use or oral administration, as claimed in claim 1, which comprises the medicinal agent being reduced to the desired particle size, mixed with a powdered mixture of 1,2-diacylglycero-3-phosphocholine and calcium chloride.

9. A process for the preparation of a pharmaceutical formulation for oral use or oral administration, as claimed in claim 1, which comprises the solution or dispersion of the medicinal agent in an organic solvent or water being mixed with a solution or emulsion of the 1,2-diacylglycero-3-phosphocholine in an organic solvent or water, and the mixture being spray-dried and the resulting spray-dried composition being compressed to form tablets or filled into capsules.

10. A process for the preparation of a pharmaceutical formulation for oral use or oral administration, as claimed in claim 1, which comprises the solution or emulsion of the 1,2-diacylglycero-3-phosphocholine in an organic solvent or water being mixed with a solution of calcium chloride in an organic solvent or water, the amount of calcium chloride being about 2–10% by weight based upon the weight of phosphocholine, and being applied in a fluidized bed, to the medicinal agent which has previously been reduced to the desired particle size, the resulting product in the form of a free-flowing powder being compressed to form tablets or filled into capsules.

11. A method of treating gastrointestinal disorders which occur in association with mucosal erosions and ulcerations in the stomach and duodenum in a mammal in need of treatment comprising administering to the mammal an effective gastrointestinal disorder alleviating amount of a 1,2-diacylglycero-3-phosphocholine in which 75–86% by weight of the acyl radicals are a mixture of fatty acid radicals comprising
    10–14% by weight of palmitic acid
    3–5% by weight of stearic acid
    8–12% by weight of oleic acid
    62–68% by weight of linoleic acid
    4–6% by weight of linolenic acid.

12. The method of treating gastrointestinal disorders as claimed in claim 11 wherein the 1-acyl radical contains
    22–26% by weight of palmitic acid
    6–9% by weight of stearic acid
    8–12% by weight of oleic acid
    50–54% by weight of linoleic acid
    4–6% by weight of linolenic acid; and the 2-acyl radical contains
    1–2% by weight of palmitic acid
    0–1% by weight of stearic acid
    8–12% by weight of oleic acid
    75–85% by weight of linoleic acid
    5–8% by weight of linolenic acid as the mixture of fatty acid radicals.

13. The method of treating gastrointestinal disorders as claimed in claim 11 which further contains up to 20% of at least one 1,2-diacylglycero-3-phosphate which is 1,2-diacylglycero-3-phosphoethanolamine, 1,2-diacylglycero-3-phosphoinositol, 1,2-diacylglycero-3-phosphoserine, or 1,2-diacylglycero-3-phosphoglycerol, in which 75–86% by weight of the acyl radicals are a mixture of fatty acid radicals comprising
    10–14% by weight of palmitic acid
    3–5% by weight of stearic acid
    8–12% by weight of oleic acid
    62–68% by weight of linoleic acid 4-6% by weight of linolenic acid.

14. The method of treating gastrointestinal disorders as claimed in claim 11 in the form of a hard gelatin capsule, which contains 50-500 mg of a 1,2-diacylglycero-3-phosphocholine per capsule.

15. The method of treating gastrointestinal disorders as claimed in claim 11 in the form of drink ampoules which contain an aqueous emulsion containing 5-60% of a 1,2-diacylglycero-3-phosphocholine.

16. The method of treating gastrointestinal disorders as claimed in claim 11 in the form of a solid formulation, in powder or tablet form, which contains a mixture of a 1,2-diacylglycero-3-phosphocholine and 2-10% of calcium chloride, relative to the phosphocholine.

17. A method of treating gastrointestinal disorders which occur in association with mucosal erosions and ulcerations in the stomach and duodenum in a mammal in need of treatment comprising administering to the mammal an effective gastrointestinal disorder alleviating amount of a 1,2-diacylglycero-3-phosphocholine in which 75-86% by weight of the acyl radicals are unsaturated fatty acid radicals or mixtures thereof with a chain length of 16, 18 or 20 carbon atoms.

* * * * *